(12) United States Patent
Ketelson et al.

(10) Patent No.: US 9,040,510 B2
(45) Date of Patent: May 26, 2015

(54) INTERACTION CONTROL OF CATIONIC BIOCIDES USING LABILE ANIONIC POLYELECTROLYTES

(75) Inventors: Howard Allen Ketelson, Dallas, TX (US); Ryan Desousa, Fort Worth, TX (US); Nissanke L. Dassanayake, Fort Worth, TX (US); Mary E. Luck, Fort Worth, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 1310 days.

(21) Appl. No.: 12/410,513

(22) Filed: Mar. 25, 2009

(65) Prior Publication Data

US 2009/0253800 A1    Oct. 8, 2009

Related U.S. Application Data

(60) Provisional application No. 61/042,186, filed on Apr. 3, 2008.

(51) Int. Cl.
*A61L 12/14* (2006.01)

(52) U.S. Cl.
CPC ............. *A61L 12/143* (2013.01); *A61L 12/14* (2013.01); *A61L 12/145* (2013.01)

(58) Field of Classification Search
CPC ...... A61L 12/14; A61L 12/143; A61L 12/145
See application file for complete search history.

(56) References Cited

U.S. PATENT DOCUMENTS

| | | | |
|---|---|---|---|
| 4,215,064 A | 7/1980 | Lindemann et al. |
| 4,361,548 A | 11/1982 | Smith et al. |
| 4,407,791 A | 10/1983 | Stark |
| 4,443,429 A | 4/1984 | Smith et al. |
| 4,503,002 A | 3/1985 | Mayhew et al. |
| 4,525,346 A | 6/1985 | Stark |
| 5,342,620 A | 8/1994 | Chowhan |
| 5,505,953 A | 4/1996 | Chowhan |
| 5,603,929 A | 2/1997 | Desai et al. |
| 5,654,262 A | 8/1997 | Desai et al. |
| 5,811,466 A | 9/1998 | Chowhan et al. |
| 6,143,799 A | 11/2000 | Chowhan et al. |
| 6,180,093 B1 | 1/2001 | De Nimai et al. |
| 6,316,506 B2 | 11/2001 | Asgharian |
| 6,365,636 B1 | 4/2002 | Chowhan et al. |
| 6,486,215 B2 | 11/2002 | Asgharian |
| 6,503,497 B2 | 1/2003 | Chowhan et al. |
| 6,528,464 B1 | 3/2003 | Xia et al. |
| 6,805,836 B2 | 10/2004 | Salamone et al. |
| 2001/0001789 A1* | 5/2001 | Asgharian |
| 2003/0096717 A1 | 5/2003 | Xia et al. |
| 2003/0130207 A1 | 7/2003 | Chowhan et al. |
| 2004/0241206 A1 | 12/2004 | Ketelson et al. |
| 2008/0312182 A1* | 12/2008 | Burke et al. |
| 2009/0196845 A1* | 8/2009 | Xia et al. |

FOREIGN PATENT DOCUMENTS

| | | |
|---|---|---|
| CA | 2 518 304 | 1/1999 |
| JP | 2000-516300 | 12/2000 |
| WO | 98/20913 | 5/1998 |
| WO | 2009/097028 | 8/2009 |

OTHER PUBLICATIONS

Coles et al., British Journal of Ophthalmology, 1984, vol. 68, pp. 549-552.*
MacKeen D L et al., 1978, "Chlorhexidine kinetics of hydrophilic contact lenses", Journal of Pharmacy and Pharmacology, Royal Pharmaceutical Society of Great Britain, 30(11):678-682.
PCT International Search Report for corresponding PCT/US2009/038152 with mailing date Mar. 3, 2010.
PCT International Written Opinion for corresponding PCT/US2009/038152 with mailing date Mar. 3, 2010.
Pelton et al., "Reversible Flocculation with Hydroxypropyl Guar—Borate, A Labile Anionic Polyelectrolyte", Langmuir, 2009, 25:192-195.
Lu et al., "Hydroxypropyl Guar—Borate Interactions with Tear Film Mucin and Lysozyme", Langmuir, 2005, 21:10032-10037.

* cited by examiner

*Primary Examiner* — Savitha Rao
*Assistant Examiner* — Gregg Polansky
(74) *Attorney, Agent, or Firm* — Michael Rein

(57) ABSTRACT

Methods of inhibiting the uptake of cationic biocides into medical devices such as contact lenses and implants are described. Methods of stabilizing emulsions containing cationic biocides are also described. In particular, the present invention provides for the use of polymers acting as labile anionic polyelectrolytes to reversibly bind cationic biocides. The reversible binding can reduce the deleterious effects of cationic biocides while maintaining biocidal activity. Preferred polymers include galactomannan and polyvinyl alcohol.

16 Claims, 3 Drawing Sheets

Colloid titration of HP-Guar/Borate interactions with Polyquad®.

United States Patent

US 9,040,510 B2

INTERACTION CONTROL OF CATIONIC BIOCIDES USING LABILE ANIONIC POLYELECTROLYTES

The present application claims benefit of U.S. Provisional Patent Application Ser. No. 61/042,186, filed on Apr. 3, 2008, the disclosure of which is specifically incorporated by reference herein.

FIELD OF THE INVENTION

The present invention is directed to methods of reversibly binding cationic biocides in solution so as to minimize their deleterious effects. In particular, the present invention is directed to methods of inhibiting the uptake of cationic biocides into medical devices such as contact lenses and implants, and of stabilizing emulsions containing cationic biocides. It has been discovered that under certain conditions, cis-diol polymers can act as labile anionic polyelectrolytes, reversibly binding cationic biocides, and inhibiting their uptake into contact lenses. The methods involve the addition of cis-diol polymers to compositions containing borate and cationic biocides such as polyquaternium-1.

BACKGROUND OF THE INVENTION

Cationic biocides are utilized in various biomedical products for their biocidal activity against a wide variety of microorganisms, as well as for their generally low toxicity in the applications for which they are used. Examples of cationic biocides include surface active quaternary ammonium compounds such as benzalkonium chloride and also polyquaternary ammonium compounds such as polyquaternium-1. Although cationic biocides are in widespread use as preservatives and antimicrobial agents in ophthalmic solutions and contact lens care solutions, they can have deleterious effects, and thus there are trade-offs associated with their use. For example, in any particular formulation a sufficient amount of the cationic biocide must be present to be effective in killing/inhibiting antimicrobial growth, yet not so much as to increase the potential for toxic effects and/or discomfort with normal use. In addition, cationic biocides, due to their ionic charge, may cause compatibility problems with other formulation components. For example, in complex formulations such as emulsions where droplet stability is critical, negatively charged droplets will aggregate in the presence of cationic molecules, thus limiting the use of this otherwise effective biocide class in these types of formulations.

Multipurpose solutions that can be used to clean, disinfect and condition lenses are available and are increasingly popular with contact lens users. Some multipurpose solutions may qualify as a "Chemical Disinfecting Solution" for use without rubbing, as opposed to conventional contact lens clearing or disinfecting solutions, which typically require a rubbing step in order to achieve a designated level of biocidal performance. Generally, these types of solutions would require a stronger level of biocidal activity, and thus either a more efficacious biocide or a higher concentration of biocide. In some instances, there is no requirement that these solutions be rinsed from the contact lens before being placed in the eye, and in other cases, the contact lens user may not always be diligent about rinsing their lenses prior to insertion, so that the solution may directly contact the ocular surface. In these types of formulations it is especially critical that the potential for toxic effects of cationic biocides be minimized.

A particular concern in case of soft contact lenses is the propensity of the biocide to be absorbed into hydrogel lens materials or adsorbed onto the lens surface, an effect commonly referred to as biocide "uptake". Typically, uptake occurs as the lens resides in the lens care solution containing the biocide. After the lens is replaced into the eye, the absorbed biocide may then be released from the lens onto the eye tissue, with the potential for ongoing irritation of sensitive ocular tissues. As the lenses may be worn for some duration, this ongoing release may have the effect of amplifying any potentially toxic or irritating effects of the biocide, as the lens is then effectively acting as a reservoir for the continued release of the biocide.

It would be advantageous to provide compositions that contain a cationic biocide yet have a reduced degree of biocide uptake into hydrogel biomaterials such as contact lenses. In this way, compositions preserved with cationic biocides, including, for example, ophthalmic and lens care compositions intended for direct application to the eye and no-rub and other lens care solutions intended for use with soft contact lenses, could be safely used without concern for increased toxicity or discomfort. It would also be advantageous to use cationic biocides as preservatives for certain pharmaceutical emulsions without impacting droplet stability. The present invention is directed to achieving these aims.

SUMMARY OF THE INVENTION

The present invention provides, in a first group of embodiments, a method of inhibiting the uptake of cationic biocides into hydrogel biomaterials, said method comprising adding to an aqueous composition containing a cationic biocide an uptake-inhibiting amount of a labile anionic polyelectrolyte. In another embodiment, the method comprises adding to a composition containing a cationic biocide and a borate an uptake-inhibiting amount of a cis-diol-containing polymer. In a preferred embodiment, the cationic biocide is a polymeric quaternary ammonium compound, and the cis-diol-containing polymer is a galactomannan. In another preferred embodiment, the cationic biocide is a polymeric quaternary ammonium compound, and the cis-diol-containing polymer is polyvinyl alcohol.

The present invention provides, in a second group of embodiments, a method of increasing the stability of an emulsion containing a cationic biocide, said method comprising adding to the emulsion an emulsion-stabilizing amount of a labile anionic polyelectrolyte. In another embodiment, the method of the present invention comprises adding to an emulsion containing cationic biocides and a borate an emulsion-stabilizing amount of a cis-diol-containing polymer.

DEFINITIONS

Figure 1:
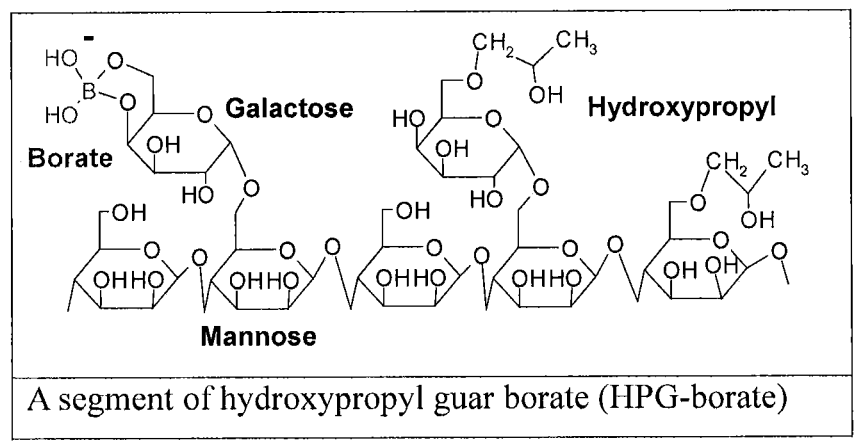
FIG. 1 is a diagram of a segment of hydroxypropyl guar borate (HPG-borate).

The term labile anionic polyelectrolyte means a polymer having anionic charges that are not permanently fixed to the polymer.

The term cis-diol polymer means a polymer having multiple hydroxyl groups, the hydroxyl groups being oriented in the same direction. Exemplary cis-diol polymers include guar and polyvinyl alcohol.

The term cationic biocide means an antimicrobial agent having fixed positive charges, and being either monomeric or polymer. Exemplary cationic biocides include those with quaternary ammonium groups such as polyquaterniums, and those with phosphonium groups.

The term uptake-inhibiting amount means an amount of cis-diol polymer sufficient to inhibit the uptake of a cationic biocide present in a composition to a hydrogel biomaterial. It is within the skill of one in the art, utilizing the teachings of the present invention, to determine the specific amount of cis-diol polymer in relation to other components of the composition, based on the desired characteristics of the composition as a whole.

The term emulsion-stabilizing amount means an amount of cis-diol polymer sufficient to increase the stability of an emulsion containing a cationic biocide relative to a reference cationic biocide-containing emulsion that does not contain a cis-diol polymer, based on emulsion stability-testing methods known in the art.

The term "pHEMA-MAA" means contact lenses comprised of poly(2-hydroxyethyl methacrylate-co-methacrylic acid). Exemplary pHEMA-MAA lenses include "Acuvue® 2" (Johnson & Johnson).

The term "an amount effective to preserve" means an amount of an antimicrobial agent effective in producing the desired effect of preserving the solutions described herein from microbial contamination, preferably an amount which, either singly or in combination with one or more additional antimicrobial agents, is sufficient to satisfy the preservative efficacy requirements of the United States Pharmacopoeia ("USP").

The term "an amount effective to disinfect", means an amount of antimicrobial agent effective in producing the desired effect of disinfecting contact lenses by substantially reducing the number of viable microorganisms present on the lenses, preferably an amount which, either singly or in combination with one or more additional antimicrobial agents, is sufficient.

The term "ophthalmically acceptable vehicle" means a pharmaceutical composition having physical properties (e.g., pH and/or osmolality) that are physiologically compatible with ophthalmic tissues.

Unless stated otherwise, an indication of a % amount of a component corresponds to weight/volume %.

DETAILED DESCRIPTION OF THE INVENTION

The method of the present invention is, in one embodiment, a method of inhibiting the uptake of cationic biocides into contact lenses, the method comprising providing to a contact lens care composition containing a cationic biocide and a borate an uptake-inhibiting amount of a cis-diol-containing polymer. In a preferred embodiment, the cis-diol-containing polymer is a galactomannan.

While not wishing to be bound by theory, it is believed that galactomannans and other polymers with cis-diol moieties such as polyvinyl alcohol will become labile anionic polyelectrolytes in the presence of borate at pH's above 7, resulting in an electrostatic interaction between the polyelectrolyte and other solutes and surfaces with positive charges, for example, cationic biocides. The electrostatic interaction is not fixed, however, due to the labile nature of the anionic charges. Surprisingly, one effect of this lability is that while the interaction is found to be effective in reducing the uptake of the cationic biocide into hydrogel biomaterials including contact lenses, the cationic biocides in solution nevertheless maintain effective antimicrobial activity.

Certain embodiments of the present invention preferably utilize galactomannan. Galactomannan is one of a number of polysaccharides containing cis-diol moieties. The types of galactomannans that may be used in the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1-4)-.beta.-D-mannopyranosyl units with alpha.-D-galactopyranosyl units attached by (1-6) linkages. With the preferred galactomannans, the ratio of D-galactose to D-mannose varies, but generally will be from about 1:2 to 1:4. Galactomannans having a D-galactose:D-mannose ratio of about 1:2 are most preferred. Additionally, other chemically modified variations of the polysaccharides are also included in the "galactomannan" definition. For example, hydroxyethyl, hydroxypropyl and carboxymethyl-hydroxypropyl substitutions may be made to the galactomannans of the present invention. Non-ionic variations to the galactomannans, such as those containing alkoxy and alkyl (C1-C6) groups are particularly preferred (e.g., hydroxylpropyl substitutions). Substitutions in the non-cis hydroxyl positions are most preferred. An example of non-ionic substitution of a galactomannan of the present invention is hydroxypropyl guar, which is preferably substituted up to about a 0.6 molar ratio.

The galactomannans of the present invention may be obtained from numerous sources. Such sources include guar gum, locust bean gum and tara gum, as further described below. Additionally, the galactomannans may also be obtained by classical synthetic routes or may be obtained by chemical modification of naturally occurring galactomannans.

Guar gum is the ground endosperm of *Cyamopsis tetragonolobus* (L.) Taub. The water soluble fraction (85%) is called "guaran" (molecular weight of 220,000), which consists of linear chains of (1-4)-.beta.-D mannopyranosyl units with alpha.-D-galactopyranosyl units attached by (1-6) linkages. The ratio of D-galactose to D-mannose in guaran is about 1:2. The gum has been cultivated in Asia for centuries and is primarily used in food and personal care products for its thickening property. It has five to eight times the thickening power of starch. Its derivatives, such as those containing hydroxypropyl or hydroxypropyltrimonium chloride substitutions, have been commercially available for over a decade. Guar gum can be obtained, for example, from Rhone-Poulenc (Cranbury, N.J.), Hercules, Inc. (Wilmington, Del.) and TIC Gum, Inc. (Belcamp, Md.).

Locust bean gum or carob bean gum is the refined endosperm of the seed of the carob tree, *ceratonia siliqua*. The ratio of galactose to mannose for this type of gum is about 1:4. Cultivation of the carob tree is old and well known in the art. This type of gum is commercially available and may be obtained from TIC Gum, Inc. (Bekamp, Md.) and Rhone-Polulenc (Cranbury, N.J.).

Tara gum is derived from the refined seed gum of the tara tree. The ratio of galactose to mannose is about 1:3. Tara gum is not produced in the United States commercially, but the gum may be obtained from various sources outside the United States.

Chemically modified galactomannans such as hydroxypropyl guar may also be utilized. Modified galactomannans of various degree of substitution are commercially available from Rhone-Poulenc (Cranbury, N.J.). Hydroxypropyl guar with low molar substitution (e.g., less than 0.6) is particularly preferred.

The structure of HP-Guar is shown in FIG. 1. Typically there are about two mannose units for every galactose; however, the detailed galactose content is determined by the guar plant. The molecular weight of the guar is a function of the galactose content and the polymannose chain length which can be lowered during processing.

Figure 2:
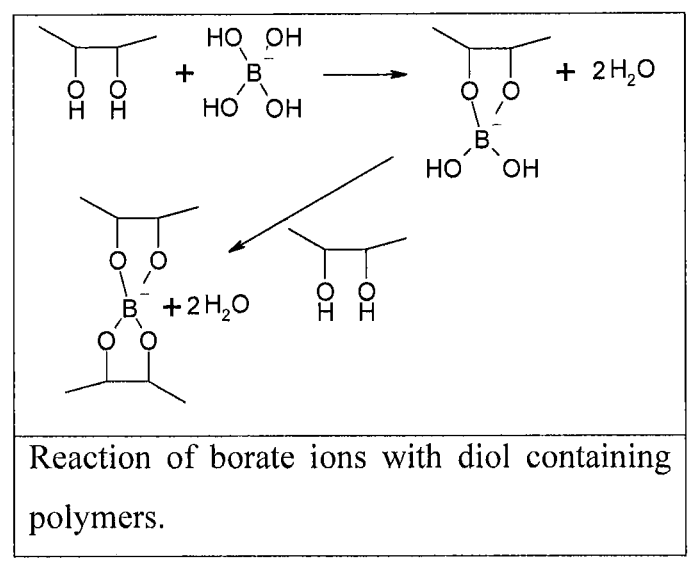
FIG. 2 is a schematic diagram of a reaction of a borate ion with a diol-containing polymer.

The reaction products between HP-Guar and boric acid are known to generate cross-links and influence the viscosity of the polymer solution. Boric acid is a Lewis acid which reacts with water to give the borate ion with the release of a proton: $B(OH)_3 + H_2O \rightarrow B(OH)_4^- + H^+$. The pKa for this reaction is 9-9.2. Borate ions can condense onto two cis-diol groups as shown in FIG. 2. When this occurs, an anionic charge is added to the chain and a crosslink is formed. Alkyl boronates such as methylboronic acid and phenyl boronic acid also bind to some carbohydrates, however, with only one reaction site, they do not give crosslinks and thus do not promote gelation. However, they can add anionic charge to the polymer. Based in part on the experiments described below, it is believed that guar becomes an anionic polyelectrolyte in the presence of borate at pH's above 7. However, due to the lability of these crosslinks, the charges are not fixed.

Certain other embodiments of the present invention preferably utilize polyvinyl alcohol (PVA). PVA is typically prepared by removing the acetal groups of polyvinyl acetate via hydrolysis. PVA is available in a number of grades, each differing in degree of polymerization, percent of hydrolysis, and residual acetate content. Such differences affect the physical and chemical behavior of the different grades. PVA can be divided into two broad categories, i.e., completely hydrolyzed and partially hydrolyzed. Those containing 4% residual acetate content or less are referred to as completed hydrolyzed. Partially hydrolyzed grades usually contain 20% or more residual acetate. The molecular weight of PVA's may vary from 20,000 to 200,000. PVA is commonly used as a viscosity enhancer, and may be used in RGP products in order to improve the comfort and wearing time of RGP products. PVA is also used as a viscosity enhancer for pharmaceutical ophthalmic compositions such as eye drops, gels or ocular inserts. In general, PVA used in ophthalmic products has an average molecular weight in the range of 30,000 to 100,000 with 11% to 14% residual acetate.

While the exact amount of cis-diol polymer in the compositions will vary according to the polymer and the formulation, compositions of the present invention generally contain cis-diol polymers at a concentration of from about 0.01% to about 1% w/v, preferably between about 0.025% to about 0.25% w/v, more preferably between about 0.05 to 0.15% w/v.

The borates which may be used in the compositions of the present invention include boric acid and other pharmaceutically acceptable salts such as sodium borate (borax) and potassium borate. As used herein, the term "borate" refers to all pharmaceutically suitable forms of borates, as well as metaborates. Borates are common excipients in ophthalmic formulations due to good buffering capacity at physiological pH and well known safety and compatibility with wide range of drugs and preservatives. Borates also have inherent bacteriostatic and fungistatic properties which provide improved preservative systems.

The compositions employed in the present invention contain a cationic antimicrobial agent, and optionally, one or more additional biocide if required for optimum preservation or disinfection. Cationic antimicrobial agents are compounds with fixed positive charges which may be either monomeric or polymeric, and derive their antimicrobial activity through a chemical or physicochemical interaction with microorganisms. Preferred polymeric cationic biocides include: polyquaternium-1, and polyquaternium-40 (poly(dimethyldiallylammonium chloride), which are polymeric quaternary ammonium compounds. These preferred antimicrobial agents are disclosed in U.S. Pat. Nos. 4,407,791 and 4,525,346, issued to Stark, and U.S. Pat. Nos. 4,361,548 and 4,443,429, issued to Smith et al., respectively. The entire contents of the foregoing publications are hereby incorporated in the present specification by reference. Other cationic antimicrobial agents suitable in the compositions and methods of the present invention include: other quaternary ammonium compounds, such as benzalkonium halides, benzethonium halide, cetrimide, phosphate quaternary compounds such as those described in U.S. Pat. Nos. 4,503,002 and 4,503,002 (Mayhew et al.), phosphobetaines as described in U.S. Pat. No. 4,215,064, pyridinium biocides, such as cetylpyridinium halides, and other biocides with fixed positive charges. Additional biocides which may be present if required may be any of those suitable for use in topical ophthalmic or lens care formulations, including, for example, biguanides such as polyhexamethylene biguanide (PHMB), polyaminopropyl biguanide (PAPB) and stabilized oxychloro compounds, such as Purite®.

Particularly preferred cationic biocides of the present invention are polymeric quaternary ammonium compounds of the structure:

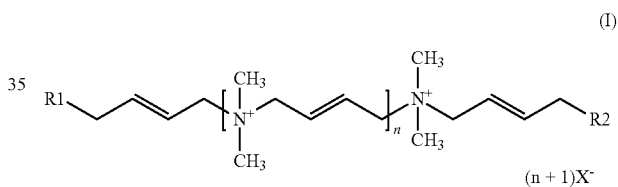

(I)

wherein:
R1 and R2 can be the same or different and are selected from: $N^+(CH_2CH_2OH)_3X^-$, $N(CH_3)_2$ or OH;
X is a pharmaceutically acceptable anion, preferably chloride; and
n=an integer from 1 to 50.

The most preferred compounds of this structure is polyquaternium-1, which is also known as Onamer M™ (registered trademark of Onyx Chemical Corporation) or as Polyquad® (registered trademark of Alcon Laboratories, Inc.). Polyquaternium-1 is a mixture of the above referenced compounds, wherein X is chloride and R1, R2 and n are as defined above.

The above-described antimicrobial agents are utilized in the methods of the present invention in an amount effective to eliminate substantially or to reduce significantly the number of viable microorganisms found on contact lenses, in accordance with the requirements of governmental regulatory agencies, such as the United States Food and Drug Administration. For purposes of the present specification, that amount is referred to as being "an amount effective to disinfect" or "an antimicrobially effective amount." The amount of antimicrobial agent employed will vary, depending on factors such as the type of lens care regimen in which the method is being utilized. For example, the use of an efficacious daily cleaner in the lens care regimen may substantially reduce the amount of material deposited on the lenses, including microorganisms, and thereby lessen the amount of antimicrobial agent required to disinfect the lenses. In general, a concentration in the range of about 0.000001% to about 0.05% by weight of one or more of the above-described antimicrobial agents will be employed. The most preferred concentration of the polymeric quaternary ammonium compounds of Formula (I) is about 0.0001% to 0.001 by weight.

The types of materials with which the compositions of the present invention may be used include various hydrogel biomaterials. Hydrogel biomaterials are polymer chain networks or crosslinked polymeric systems that contain water in their hydrated state. Conventional hydrogel lens materials are made from such hydrophilic monomers s 2-hydroxyethyl methacrylate (HEMA), glyceryl methacrylate and N-vinylpyrrolidone (NVP). These materials typically provide a high degree of flexibility and a significant water content, in many ways emulative of biological tissue. Silicone hydrogels represent another class of hydrogel material. Hydrogel biomaterials of all these and other various types are used to comprise contact lenses. All of the foregoing hydrogel types are found in various types of soft contact lenses. The present invention may be used with a variety of types of contact lenses, such as hard, soft, rigid and soft gas permeable, and silicone lenses. Another type of contact lens is the rigid type, including rigid-gas-permeable (RPG) material.

The compositions employed in the present invention will contain other ingredients. Such ingredients may include antimicrobial/preservative agents, tonicity adjusting agents, buffers and chelating agents. Other polymer or monomeric agents such as polyethylene glycol, and glycerol may also be added for special processing. Tonicity adjusting agents useful in the compositions of the present invention may include salts such as sodium chloride, potassium chloride and calcium chloride, and polyols such as mannitol and sorbitol; non-ionic tonicity agents may include propylene glycol and glycerol; chelating agents may include EDTA and its salts; and pH adjusting agents may include hydrochloric acid, Tris, triethanolamine and sodium hydroxide. Suitable anti-microbial agents/preservatives are discussed more fully below. The above listing of examples is given for illustrative purposes and is not intended to be exhaustive. Examples of other agents useful for the foregoing purposes are well known in ophthalmic and contact lens care formulation and are contemplated by the present invention.

The following examples further illustrate various embodiments of the invention. These examples are provided to aid in the understanding of the invention and are not to be construed as limitations thereof.

EXAMPLE 1

Colloid Titration in Support of an Interaction Between HP-Guar/Borate and a Cationic Biocide (Polyquad®)

Figure 3:
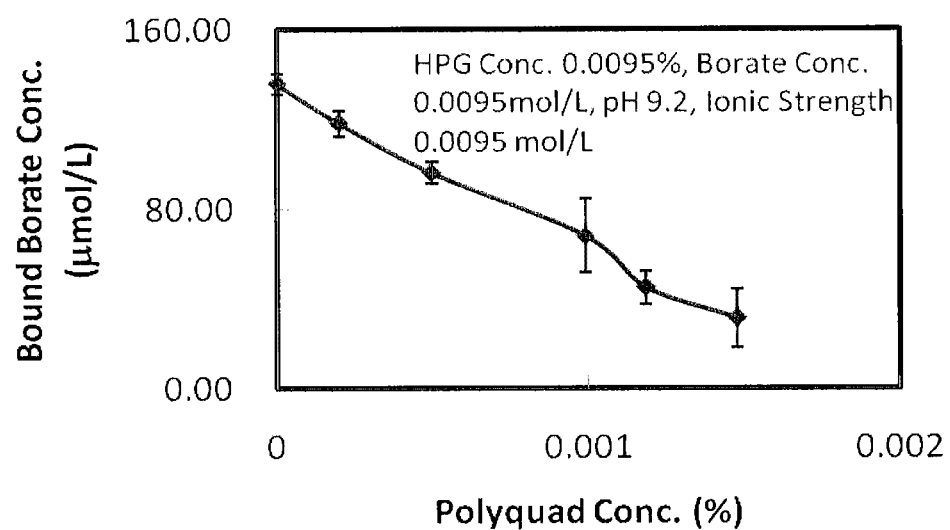
FIG. 3 is a graph of colloid titration of HP-Guar/Borate interactions with Polyquad.

Streaming potential titration was performed using a Mutek PCD T3 titrator with a Mutek PCD 03 streaming current detector (SCD). The detector has a cylindrical cell and a piston that are made from polytetrafluoroethylene (PTFE). The polyelectrolyte in the sample adsorbs onto the wall of the cell and the piston surface. The piston oscillates in the cell vertically squeezing the fluid. Polyelectrolytes are separated from the counterions by the flow which creates a streaming potential that is detected by two gold electrodes on the wall of the cell. Polyelectrolyte is titrated by polyelectrolyte with counter charge. In a typical experiment, 10 mL of sample was loaded into the cylindrical cell using 0.001 mol/l poly(diallyldimethylammonium chloride) (PDADMAC) as titrant. All experiments were performed three times at 25° C. at a pH of 9.2. The results of experiments conducted using HP Guar, borate and Polyquad® are shown in FIG. 3. The results demonstrate that with the addition of Polyquad®, the bound borate concentration decreased (shown along the x-axis), indicating an increasing interaction between HP-Guar/Borate and Polyquad®. These results support a conclusion that the decrease in bound borate concentration is a reflection of Polyquad® binding to the HP-Guar borate-bound sites.

EXAMPLE 2

Reduction of Polyquad® Uptake into Polyhydroxyethyl Methacrylate-Methacrylate (pHEMA-MAA) Acuvue 2 Lenses Using HP-Guar Table 1 shows the vehicle used to explore the dose response of HP-Guar on the uptake of Polyquad® into Acuvue 2 lenses.

TABLE 1

| Composition of formulation vehicle for lens uptake studies. | |
|---|---|
| Formulation Chemicals | % wt/vol |
| Polyquad ® | 0.0002 |
| Hydroxypropyl Guar 8A | 0.025-0.1 |
| Sorbitol | 0.4 |
| Propylene Glycol | 1.0 |
| Sodium Chloride | 0.3 |
| Tetronic 1304 ® | 0.1 |
| Sodium Borate Decahydrate | 0.6 |
| EDTA | 0.05 |
| pH | 8.0 |

The lens uptake data is shown in Table 2. Formulation services D, E, F and A were modified by increasing the HP-Guar concentration from 0.025% to 0.1% using a targeted Polyquad® concentration of 2 ppm and pH 8.0. Increasing the HP-Guar from 0.025% to 0.1% decreased the Polyquad® uptake in the Acuvue 2 lenses from 0.7 μg/lens to 0.34 μg/lens. This data is provided in Table 2.

TABLE 2

| Effect of HP-Guar on Polyquad ® lens update after 2 cycles. | | |
|---|---|---|
| Formulation | HP-8A Concentration | Acuvue 2 Lens Uptake (μg/lens) |
| D | 0.025 | 0.7 |
| E | 0.05 | 0.6 |
| F | 0.074 | 0.5 |
| A | 0.1 | 0.34 |

These results demonstrate that HP-Guar can be used to the lower Polyquad® uptake in Acuvue 2 (Group IV) lens material. The uptake reduction demonstrated likely results from HP-Guar acting as an anionic polyelectrolyte in the presence of borate.

EXAMPLE 3

Effect of HP-Guar on Disinfection Activity and Lens Uptake of Polyquad®

Additional studies were pursued in order to explore lowering the lens uptake values further by increasing the HP-Guar concentration. Table 3 shows that the uptake data for HP-Guar concentrations of 0.1%, 0.12% and 0.14% were 0.33 µg/lens, 0.29 µg/lens and 0.24 µg/lens, respectively. Disinfection screen data is also provided in Table 3. The control formulation G is the marketed Opti-Free® Rinsing, Disinfection, and Storage Solution. The data shows that the secondary screen disinfection criteria was met.

TABLE 3

Effect of HP-Guar on the Disinfection Screen and Lens Uptake of Disinfecting Solutions Containing Polyquad ®.

| Component | A | B | C | G[a] |
|---|---|---|---|---|
| Polyquad ® | 0.00025 | 0.00025 | 0.00025 | |
| TETRONIC 1304 ® | 0.1 | 0.1 | 0.1 | |
| HP Guar 8A | 0.1 | 0.12 | 0.14 | |
| Propylene glycol | 1.0 | 1.0 | 1.0 | |
| EDTA | 0.05 | 0.05 | 0.05 | |
| Sorbitol | 1.0 | 1.0 | 1.0 | |
| Sodium chloride | 0.3 | 0.3 | 0.3 | |
| Sodium borate | 0.6 | 0.6 | 0.6 | |
| pH | 8.0 | 8.0 | 8.0 | |
| Uptake (Acuvue 2) 2 cycles µg/lens | 0.33 | 0.29 | 0.24 | |

| Organism | Time (hrs) | A | B | C | G |
|---|---|---|---|---|---|
| C. albicans | 6 | 0.2 | 0.1 | 0.1 | 0.00 |
| $1.5 \times 10^{6b}$ | 24 | 1.6 | 1.6 | 1.5 | 0.9 |
| S. marcescens | 6 | 3.9 | 3.4 | 3.0 | 1.3 |
| $9.0 \times 10^5$ | 24 | 4.5 | <u>6.0</u> | 3.6 | 2.4 |
| S. aureus | 6 | 3.1 | 2.9 | 2.9 | 2.4 |
| $8.2 \times 10^2$ | 24 | 4.1 | 3.6 | 3.3 | 4.1 |

[a]Opti-Free ® Rinsing, Disinfection, and Storage Solution.
[b]Inoculum control count.
[c]Underlined number indicates not survivors (<10 CFU/mL) recovered.

EXAMPLE 4

The Uptake of Polyquad® in Acuvue 2 Lenses in the Presence of PVA and Borate at pH 7.8 as a Function of Sorbitol Concentration In the formulation series shown in Table IV the use of a different polymer, polyvinyl alcohol (PVA), which also reacts with borate, was evaluated, along with the effect of sorbitol on the PVA binding with Polyquad®. Sorbitol will compete with PVA and influence the PVA-borate interaction. Increasing the concentration of sorbitol was expected to lead to reduced reactions of borate with PVA, and lead to a corresponding increase in Polyquad® lens uptake. Formula A is the control solution without PVA. The lens uptake using this solution was 2.3 µg/lens. Following addition of 0.05% PVA the uptake decreased to 1.0.

TABLE 4

The Uptake of Polyquad ® in Acuvue 2 Lenses in the Presence of Polyvinyl Alcohol and Borate at pH 7.8 as a Function of Sorbitol Concentration.

| Chemical (% wt/% vol) | A | B | C | D |
|---|---|---|---|---|
| Polyquad | 0.0005 | 0.0005 | 0.0005 | 0.0005 |
| AL-6289 | 0.0005 | 0.0005 | 0.0005 | 0.0005 |
| Propylene Glycol | 1.0 | 1.0 | 1.0 | 1.0 |
| Boric Acid | 0.4 | 0.4 | 0.4 | 0.4 |
| Sodium Chloride | 0.3 | 0.3 | 0.3 | 0.3 |
| Sorbitol | 1 | 0 | 0.5 | 0.75 |
| Tetronic 1304 | 0.05 | 0.05 | 0.05 | 0.05 |
| EDTA | 0.05 | 0.05 | 0.05 | 0.05 |
| PVA 47K | — | 0.05 | 0.05 | 0.05 |
| pH | 7.79 | 7.79 | 7.8 | 7.8 |
| Obs 36 h Turbidity | Clear | Hazy | Slight Haze | Faint Haze |
| Polyquad Uptake, µg/lens | 2.3 | 1.0 | 1.8 | 2.1 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

The invention claimed is:

1. A method of using a galactomannan to inhibit uptake of a cationic biocide into hydrogel biomaterials, the method comprising adding to a composition containing a cationic biocide and a borate a galactomannan in an amount to form a concentration between 0.025 to 0.074% w/v, wherein the composition is adapted for use with hydrogel biomaterials.

2. A method according to claim 1, wherein the pH of the composition is greater than 7.

3. A method according to claim 1, wherein the galactomannan is hydroxypropyl guar.

4. A method according to claim 3, wherein the concentration of hydroxypropyl guar is 0.05%.

5. A method according to claim 1, wherein the cationic biocide is a polymeric quaternary ammonium compound.

6. A method according to claim 5, wherein the polymeric quaternary ammonium compound is polyquaternium-1.

7. A method of reversibly binding cationic biocides in solution to inhibit uptake of the biocide into hydrogel biomaterials, the method comprising adding hydroxypropyl guar in an amount to form a concentration between 0.025 to 0.074% w/v to a composition containing a cationic biocide and a borate.

8. A method according to claim 7, wherein the pH of the composition is greater than 7.

9. A method according to claim 8, wherein the pH of the composition is not greater than 8.

10. A method according to claim 7, wherein the cationic biocide is a polymeric quaternary ammonium compound.

11. A method according to claim 10, wherein the polymeric quaternary ammonium compound is polyquaternium-1.

12. A method according to claim 8, wherein the cationic biocide is a polymeric quaternary ammonium compound.

13. A method according to claim 12, wherein the polymeric quaternary ammonium compound is polyquaternium-1.

14. A method according to claim 13, wherein the concentration of hydroxypropyl guar is about 0.05 w/v %.

15. A method according to claim 7, wherein the concentration of hydroxypropyl guar is about 0.05 w/v %.

16. A method according to claim 1, wherein the hydrogel biomaterial is a soft contact lens.

* * * * *